United States Patent [19]

Wagner

[11] Patent Number: 4,681,442
[45] Date of Patent: Jul. 21, 1987

[54] METHOD FOR SURFACE TESTING

[75] Inventor: Dietmar Wagner, Gärtringen, Fed. Rep. of Germany

[73] Assignee: International Business Machines Corporation, Armonk, N.Y.

[21] Appl. No.: 713,077

[22] Filed: Mar. 18, 1985

[30] Foreign Application Priority Data

May 14, 1984 [EP] European Pat. Off. ........ 84105425.7

[51] Int. Cl.$^4$ .............................................. G01N 2/88
[52] U.S. Cl. ..................................... 356/237; 250/63; 250/572; 356/239
[58] Field of Search ............... 356/237, 239, 430, 431, 356/446; 250/562, 563, 572

[56] References Cited

U.S. PATENT DOCUMENTS 4,468,120  8/1984  Tanimoto et al. .................. 356/237
4,541,715  9/1985  Akiyama et al. .................... 356/237

FOREIGN PATENT DOCUMENTS 122905  9/1981  Japan .................................. 356/237

OTHER PUBLICATIONS

Ross, "Optical Scanning System for Defect Detection", IBM Tech. Discl. Bull. vol. 20, No. 9, p. 3431, 2/78.
Rapa, "Inspection System for Particulate Contamination" IBM Tech. Discl. Bull. vol. 20, No. 11A, p. 4359, 4/78.

Primary Examiner—Davis L. Willis
Assistant Examiner—Matthew W. Koren
Attorney, Agent, or Firm—Francis J. Thornton

[57] ABSTRACT

This teaches a method and device for testing of the surface of a transparent object such as a photolithographic mask in which respective recordings with darkfield reflection illumination and darkfield transmission illumination is made, and the intensities measured are compared to form a different image, in which defects are characterized by high local levels of light intensity. Both recordings can be generated in a point-by-point mode if the surface is scanned by a focussed laser beam. In another embodiment, two recordings of the entire surface are digitized, and examined arithmetically for local image differences. Surfaces of opaque bodies can also be examined with the difference image of two darkfield reflection recordings made at different angles of illumination.

8 Claims, 7 Drawing Figures

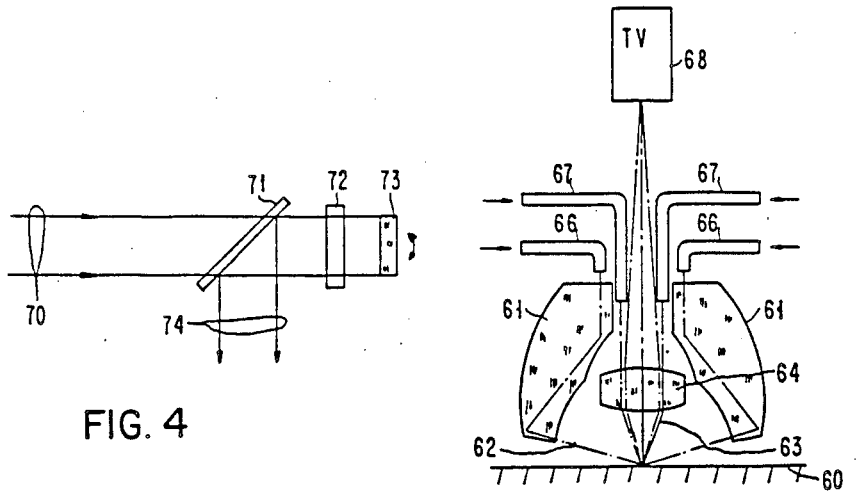
FIG. 4
FIG. 6
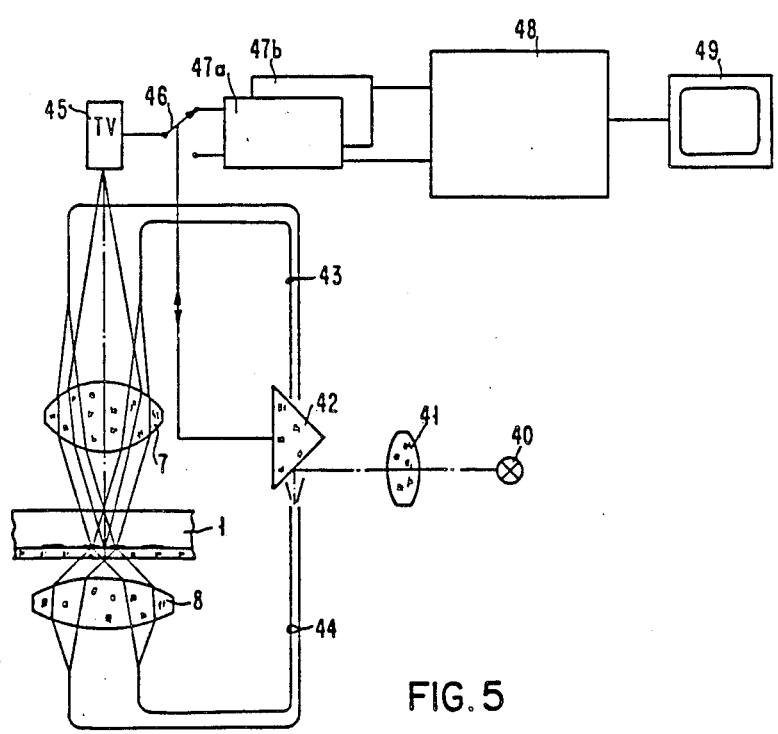
FIG. 5

METHOD FOR SURFACE TESTING

DESCRIPTION

The invention relates to a method for testing surfaces and devices for carrying out said method. The invention is preferably useful for testing photolithographic masks and semiconductor wafers for defects.

Inspecting the surfaces for defects, with diameters in the submicron range, is necessary for numerous modern manufacturing processes; examples are the inspection of photolithographic masks, optical surfaces, or polished wafer surfaces.

The demands made on the inspection equipment used are increasing, particularly, with respect to photolithographic masks, where the regular structures of the mask itself (e.g. conductor width and spacing) enter the range of one micrometer and less. If the smallest structures resolved by the mask are e.g. 1.5 $\mu$m, defects of the mask with a diameter of 0.5 $\mu$m and more have to be located; with structures of 0.75 $\mu$m the detection limit is reduced accordingly to 0.25 $\mu$m. To ensure a high yield during the photolithographic process, all masks used have to be regularly checked for defects in that range since new defects can form continuously owing to grains of dust, etc.

The appearance of new defects on an already tested mask can be reduced if, at a distance of some millimeters over the mask layer proper a transparent protective foil (a so-called pellicle) is provided which collects grains of dust and other contaminations. In the imaging of the mask in photo-optical systems with a high resolution, this protective foil will then be outside the very narrow focal depth region so that the dust particles on the pellicle do not affect the first image. However, a thus protected mask can no longer be tested with the necessary resolution for defect particles which may have appeared on the actual mask plane in spite of the protective foil. The high resolutions needed in the submicron range require optical systems for inspection, e.g. darkfield microscopes of a very high numerical aperture, whose focal length will be smaller than the distance between mask and protective foil. Furthermore, in modern photolithographic masks with their very small structures it is getting increasingly difficult to differentiate between regular patterns and defect particles. In the visual inspection of such masks therefore defects are frequently overlooked; it is furthermore very time-consuming, and a strain for the eyes.

For the above reasons, the hitherto known methods and devices for inspecting photolithographic masks can find, on protective foil-equipped masks, only those defects whose diameter is greater than approximately 3$\mu$ (although, with masks without protective foils, particles of up to 0.5$\mu$ can be detected). Examples for such known devices are as follows:

optical subtraction methods where the mask to be tested is scanned simultaneously with a reference mask, methods comprising digital image processing, where
the mask to be tested is converted into a digital image which is then compared with a stored digital image, or analyzed in accordance with the methods of image processing.

It is therefore the object of the present invention to provide a testing method of the above specified type which is applicable in particular to the inspection of photolithographic masks, which reliably finds defects in the submicron range and permits conclusions as to their approximate diameter, which permits speedy implementation and can be carried out automatically. Furthermore, devices for carrying out the method will be presented.

The basic idea of the present invention consists in observing a surface under two different types of illumination, and in comparing the two images so obtained. Since the optical characteristics, e.g. the scattering properties of the defects, differ from the regular mask structures, this comparison permits a clear definition of defects. As a preferred type of illumination for transparent bodies, the darkfield reflection where the regular structures (e.g. edges) are emphasized is used on the one hand, and on the other the darkfield transmission which stresses the defects. To define the image differences of the two types of illumination, the mask can be successively recorded by a television camera (with a correspondingly precise adjustment) for a subsequent digital image processing. According to another embodiment, the mask is scanned by a focussed laser beam, and the darkfield signal produced at any point in reflection and transmission is simultaneously registered, and electronically evaluated. For opaque bodies with reflecting surfaces, darkfield transmission recordings under different angles of observation are made.

The devices for implementing the method permit automatic inspection with relatively short processing times. For laser scanning, defects of approximately 0.3 $\mu$m can be resolved also for masks with protective foils.

Embodiments of the invention will now be described in detail with reference to drawings wherein:

FIG. 4 shows an example for an oscillating mirror of high deflection frequency for a scanning arrangement in accordance with FIG. 3.

FIG. 5 shows another embodiment of the present invention with digital processing of the darkfield transmission and the darkfield reflection images of a photolithographic mask.

FIG. 6 shows the schematic representation of another embodiment of the invention, where the reflecting surface of an opaque body is examined for defects.

Figure 1:
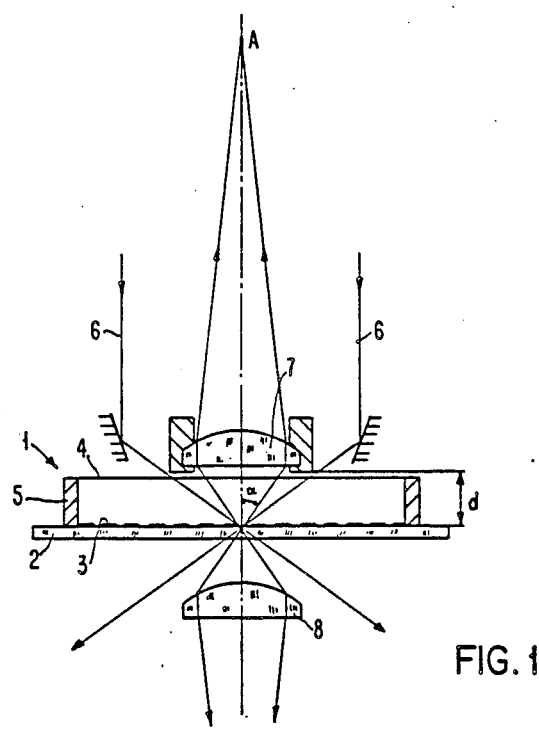
FIG. 1 shows the basic beam path for the darkfield reflection and darkfield transmission inspection of a photolithographic mask with a protective foil.

FIG. 1 depicts the basic beam path in the optical inspection described here of a photolithographic mask 1, which consists of a transparent substrate carrier 2 with an opaque pattern 3 deposited thereon, e.g. of chromium, and a protective foil 4 carried by a ring 5 at a distance of several millimeters over the mask. The smallest characteristic dimensions of the chromium pattern 3 may be, for example 1.5 $\mu$m less for present-day masks. Such masks are still visually inspected for defects with the darkfield reflection illumination being selected as a preferable illumination arrangement. For that purpose, the light scattered by light beams 6 impinging in oblique direction onto the mask surface is collected in a microscope objective 7. The minimum working distance d of objective 7 from the substrate 2 surface to be sharply defined is determined for a protective foil-equipped mask by the height of ring 5 which is usually some millimeters. However, if there is a great working distance d (and a correspondingly great focal length of objective 7) the result is a relatively small numeric aperture N.A.=sinα; this in turn limits the image resolution by objective 7, i.e. the distance Δx of two resoluble points which is defined by the so-called Rayleigh criterion:

$$\Delta x = \frac{0.61\lambda}{N.A.}$$

An aperture sufficient for the resolution of defect particles with diameters amounting to approximately 0.3 μm would on the other hand require working distances of about 1 mm or less.

Figure 2A:
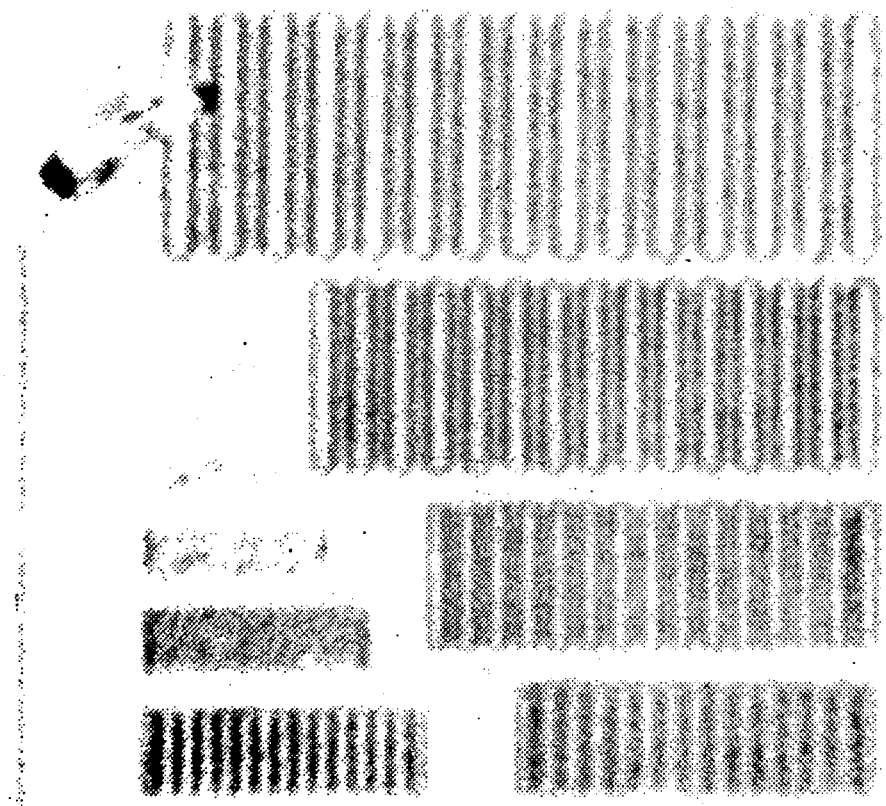
FIG. 2A is an example for a darkfield reflection image of a photolithographic mask.

FIG. 2A depicts a photograph of a photolithographic mask with the above described darkfield reflection illumination, with a relatively small enlargement. The regular mask structures, particularly the edges, appear very clearly with this kind of illumination, while the (point-shaped) defects are very difficult to detect.

That part of FIG. 1 which is represented under glass plate 2 depicts the basic beam path for a second kind of illumination, the so-called darkfield transmission illumination. An objective 8 collects the light which has been scattered by scattering elements on the surface of glass plate 2, and which passes through plate 2 itself. The light (corresponding to beams 6) used for illumination however goes past objective 8.

Figure 2B:
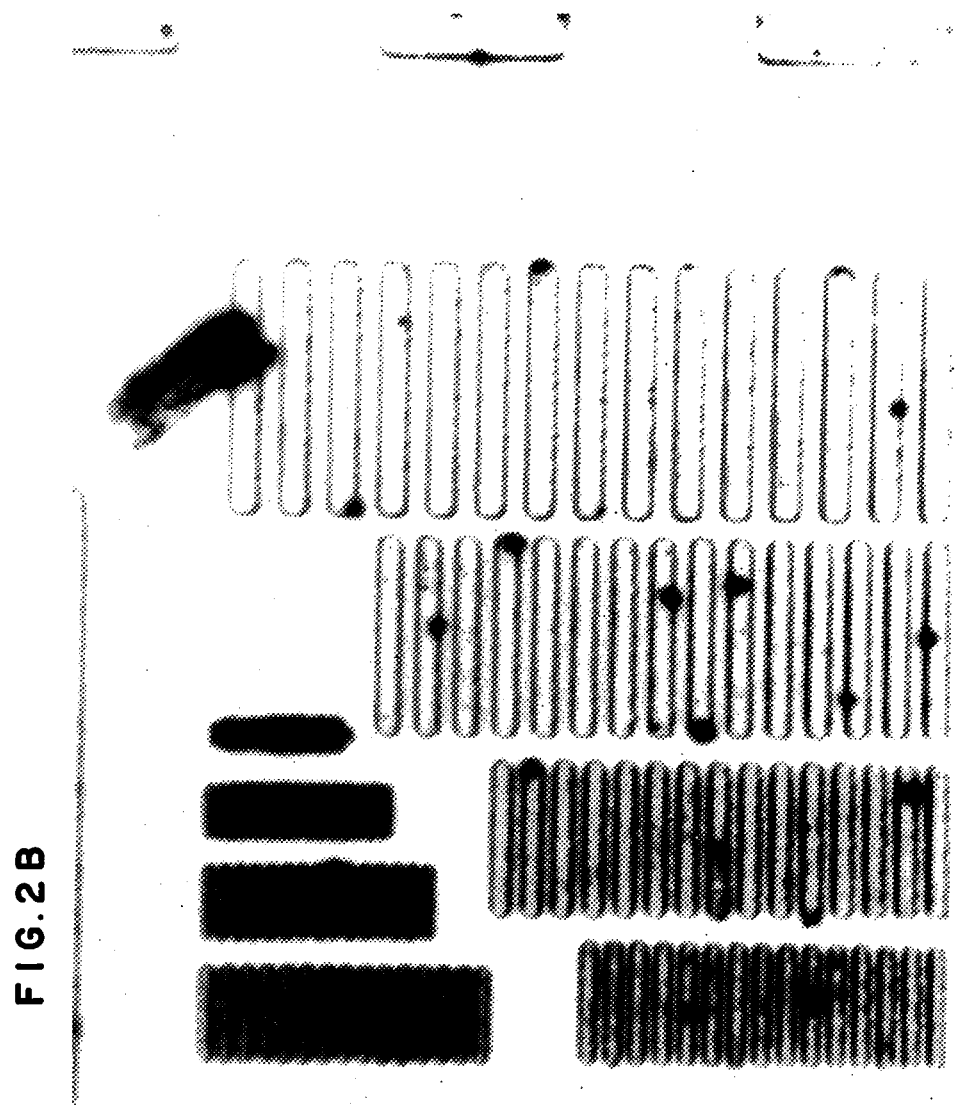
FIG. 2B is a darkfield transmission image of the same mask as in FIG. 2A.

If now the same mask as in FIG. 2A is recorded with the darkfield transmission arrangement the result is FIG. 2B where the regular mask structures are less emphasized but the mask defects appear as very bright points. The recording of FIG. 2B has been effected with the same enlargement (∼500) and a slightly wider aperture than in FIG. 2A.

The obvious difference between the two recordings in FIG. 2A and FIG. 2B is due on the one hand to the different optical scattering at the edges, and small particles on the other. The latter show a clear forward scattering (a so-called Mie scattering) as a function of the particle size, which is particularly striking in the darkfield transmission.

For easy and particulary for automatic evaluation of the various scattering centers, and consequently for differentiating between regular mask structures and defects the darkfield reflection and darkfield transmission recordings are subtracted. If this subtraction results in strong local differences this means that there are defect particles. The extent of the differences permits a rough conclusion concerning the defect size (since the scattering characteristics of small particles depend on the particle size).

For the comparison suggested here the prior art methods for detecting differences between two images can be used. These include, to give an example, strictly optical processes where the two images are projected one over the other, either simultaneously with respectively multi-coloured illumination (and thus coloured emphasizing of the non-identical image parts), or alternatingly for locating non-identical image parts as flickering points. Digital processing methods are possible, too, where both images are digitized, and the subsequent comparison is carried out arithmetically with the coloured or grey values found.

Figure 3:
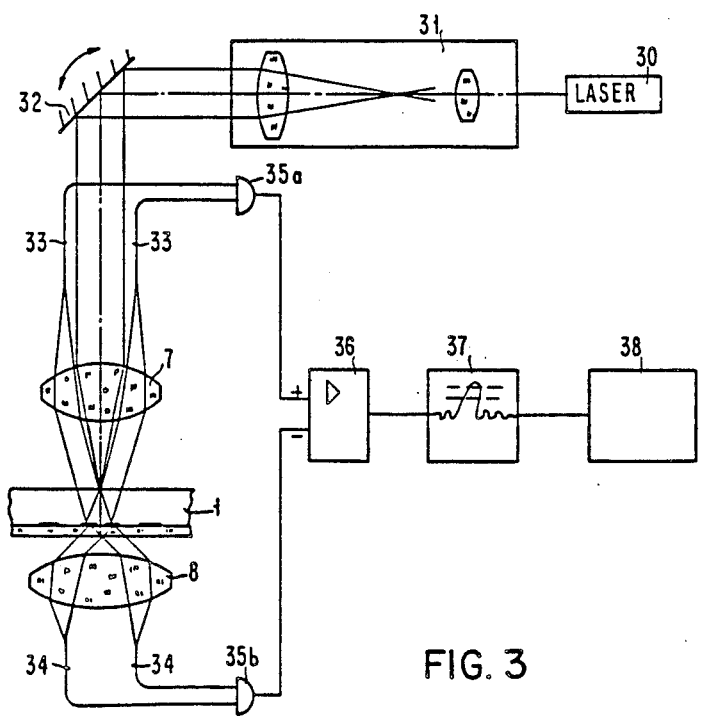
FIG. 3 shows the schematic representation of an embodiment of the present invention with a focussed bundle of laser beams scanning the mask.

Particularly advantageous devices for carrying out the comparator process described here are schematically represented in FIGS. 3 and 5. According to FIG. 3, the mask with protective foil 1 is scanned point-wise by a focussed laser beam which emanates from a laser 30 and, after having passed through a beam expander 31, is deflected by an oscillating mirror 32 into focussing objective 7. For collecting the reflected light scattered on the mask surface, light wave conductors (optical fibers) 33 are used which are provided in an annular arrangement behind objective 7 in such a manner that they can absorb only the non-regularly reflected light passing through the objective. A microscope objective with such an arrangement of optical fibers is described e.g. in European Pat. No. 11 709. All optical fibers 33 are connected toward a photodiode 35a whose output signal is used as an input for a difference circuit 36. Under mask 31, a second objective 8 is provided in accordance with FIG. 1, which is also equipped with an annular arrangement of optical fibers 34.

To alter the angle of illumination, the ends of the optical fibers can be shifted in parallel to the optical axis of the objectives. Other kinds of darkfield illumination are possible, e.g. with mirrors.

The angle for the darkfield illumination should be adjustable for finding the optimum contrast between reflection and transmission recording. An angle of illumination close to the darkfield observation angle will ensure a good contrast in many cases.

Optical fibers 34 are connected to a photodiode 35b supplying a second output signal for difference circuit 36. The output signal of difference circuit 36 is connected toward a threshold circuit 37 which finds out whether the difference of the optical signals of the point that is just being scanned exceeds a predetermined adjustable value, and thus indicates the existence of a defect. Located defects can then be marked in a storage 38 which is addressed in accordance with the respective position of the focussed laser beam on the mask surface.

The mask is scanned in a raster mode, either with two series-arranged oscillating mirrors (32), or with one single mirror 32 and a mechanical shifting of mask 1 in the coordinate direction vertical thereto.

The arrangement according to FIG. 3 therefore does not record two successive images, but of each individual point of the mask the darkfield reflection and darkfield transmission signal are determined simultaneously. The high illumination made available by a laser permits an excellent signal to noise ratio which can be further improved by using sensitive photoamplifiers instead of photodiodes 35. As the sensitivity of the method is mainly determined by the signal to noise ratio (rather than by the optical resolution) defects with a size of up to approximately 0.3 μm can be located; furthermore, there can be a rough classification of the particle size in accordance with the size of the output signal.

The time required for the complete testing of a mask (with diameters of up to 10 cm) substantially depends on the deflection frequency of oscillating mirror 32. This frequency is determined by the natural resonance of the oscillation, and consequently by the accelerated mass of the mirror, and is 4 kcps maximum. The oscillation frequency can be doubled if an oscillating mirror is used which is not oriented in the angle bisectrix, but vertically to the impinging beam. The mirror diameter is then smaller by a factor of $\sqrt{2'}$, and consequently the mirror mass by a factor of 2.

FIG. 4 represents such an arrangement, where a (polarized) laser beam (70) can be deflected in direction 74. For that purpose, beam 70 passes first through a polarizing beam splitter 71 arranged at 45° relative to the beam axis, and reaches via a λ/4 plate 72 the reflecting surface of oscillating mirror 73 which has to be of a size sufficient for reflecting the entire impinging beam 70. The reflected light is deflected at beam splitter 71, since it has twice passed through λ/4 plate 72, and its direction of polarization has thus been rotated by 90°. In the present arrangement, the angles of deflection of oscillating mirror 73 are small (approximately 7°) so that even in case of a maximum deflection there can be no disturbancies of the beam path by oblique angles.

FIG. 5 represents a further example for an automatic device of mask inspection; its optical structure substantially corresponds to that of FIG. 1. The obliquely impinging light beams for the darkfield transmission and darkfield reflection illumination are directed through optical fibers 43 and 44, respectively, which as in the case of FIG. 3 are arranged annularly around objectives 7 and 8. The darkfield transmission and darkfield reflection illumination are periodically alternated, e.g. by placing either the group of optical fibers 43, or the group of optical fibers 44 into the beam path of a lamp 40 with lens 41 arranged in front thereof. According to FIG. 5, this switching can be effected by a prism 42 which is shifted upward and downward, and whose mirrored lateral surfaces reflect the light of the lamp into the respective optical fibers. Here, too, the ends of the optical fibers are behind the imaging optics (7 and 8, respectively) so that the exiting light passes through the optics.

The two darkfield images are observed by a television camera 45 which via an alternating switch 46 can be selectively connected to one of two image storages 47a, 47b. The position of alternating switch 46 is synchronized with that of deflection prism 42. The two digital images in memories 47 can then be passed on for evaluation to an image processor 48 which can detect local image differences by means of known digital processing methods. For that purpose, a correspondingly programmed computer 48 can be used whose results appear on a display monitor 49.

In the arrangement according to FIG. 5 it has to be made sure that the mask does not move during the period between the two recordings with different illumination, since this could simulate mask defects. The optical resolution of the arrangement according to FIG. 5 is lower than if a scanning focussed laser beam had been used, but, with an advantageous signal to noise ratio in the video signal, particles can still be located which are below the actual optical resolution, for they increase the local signal level, so that these signals can be separated from other signals provided there is a sufficiently high signal to noise ratio. The advantage of the arrangement according to FIG. 5 consists in that for evaluating the image differences known digital methods and electronic equipment can be employed.

The process described above with reference to examples for testing the surface of transparent bodies can also be applied to the surfaces of opaque bodies. For that purpose, a further darkfield reflection recording is made instead of the darkfield transmission recording, and the angle of incidence of the illuminating light is altered compared with the first recording. Regular structures, e.g. edges, and defects, e.g. dust grains, differ clearly in their scattering properties with suitably selected kinds of illumination so that defects can again be located by subtracting the darkfield recordings obtained.

FIG. 6 represents an example of a device for testing the surface of opaque bodies, in accordance with the method suggested here. Of surface 60, e.g. the polished surface of a semiconductor wafer, two darkfield reflection recordings are alternatingly made and, via objective 64, are imaged on a television camera 68 for further processing (subtraction). The two darkfield reflection illuminations 62 and 63 differ in their angle of incidence, and are produced by optical fibers 66 and 67, respectively, arranged annularly round the optical axis. Optical fibers 67 for darkfield illumination 63 impinging at an acute angle are arranged, in the present case, behind imaging object 64. Darkfield illumination 62 impinging on surface 60 at a wide angle exits from optical fibers 66 arranged annularly round the optical axis, and reaches a cardioid condensor 61 where the beams are repeatedly reflected until upon their exiting they have the desired angle of inclination relative to the optical axis.

The two entry angles for the darkfield illuminations are selected in such a manner that for regular structures (edges) on the one hand, and defect particles on the other maximum differences in the two darkfield recordings are obtained. The recordings are then evaluated in the manner described above.

What is claimed is:

1. A method of testing surfaces of transparent objects for the presence of defects thereon comprising the steps of:
   impinging light on a surface of an object to be tested at an angle to the surface,
   said light being partially reflected as a first light beam by the surface, and partially transmitted as a second light beam through the object, and partially scattered by defects on the surface, said scattered light being both partially reflected as a third light beam and partially transmitted as a fourth light beam through the object,
   collecting and recording the first and third light beams,
   collecting and recording the second and fourth light beams, and
   processing the recorded second and fourth light beams and the recorded first and third light beams and detecting the differences therebetween to locate the defects on the surface.

2. The method of claim 1 wherein said impinging light impinges on said surface at an oblique angle to the surface.

3. The method of claim 1 wherein the differences in intensity of the second and fourth light beams and the first and third light beams is measured and used to determine the size of the located defect.

4. The method of claim 1 wherein said inpinging light comprises a scanning focussed laser beam and is processed as the light scans across the surface.

5. A method of testing the surface of an opaque object for the presence of defects thereon comprising the steps of:
   impinging light from a first source on the surface to be tested at an acute angle to the surface,
   impinging light from a second source on the surface to be tested at an oblique angle to the surface,
   the light from both first and second sources being partially reflected as first and second light beams by the surface and by defects thereon, and partially scattered by said defects on the surfaces,
   collecting and separately recording all the reflected light from both said first and second sources, processing the recorded reflected light from the first source and the second source and detecting the differences between the reflected light from the first source and the reflected light from the second source to locate the defects on the surface.

6. The method of claim 5 wherein said impinging light from said first source is directed on said surface via a cardioid condenser.

7. A method of testing a surface of a transparent object for the presence of defects thereon comprising the steps of:

impinging light from a first light beam on the surface to be tested at an angle to the surface, said light being partially reflected by the surface and objects thereon, and partially scattered by said objects on the surfaces, collecing and recording the reflected light, turning off said impinging light, transmitting light through the object to the surface to be tested, collecting and recording the transmitted light, turning off said transmitting light, and process the recorded transmitted light and the recorded reflected light and detecting the differences therebetween to locate defects on the surface.

8. The method of claim 7 wherein said impinging light impinges on said surface alternate with the transmitted light.

* * * * *